(12) United States Patent
Volp

(10) Patent No.: US 12,042,667 B2
(45) Date of Patent: Jul. 23, 2024

(54) DEVICE FOR IMMOBILIZING THE HEAD OF A PATIENT

(71) Applicant: IT-V MEDIZINTECHNIK GMBH, Innsbruck (AT)

(72) Inventor: Markus Volp, Innsbruck (AT)

(73) Assignee: IT-V MEDIZINTECHNIK GMBH, Innsbruck (AT)

(*) Notice: Subject to any disclaimer, the term of this patent is extended or adjusted under 35 U.S.C. 154(b) by 847 days.

(21) Appl. No.: 17/043,716

(22) PCT Filed: Apr. 24, 2019

(86) PCT No.: PCT/EP2019/060440
§ 371 (c)(1),
(2) Date: Sep. 30, 2020

(87) PCT Pub. No.: WO2019/211132
PCT Pub. Date: Nov. 7, 2019

(65) Prior Publication Data
US 2021/0023392 A1 Jan. 28, 2021

(30) Foreign Application Priority Data

May 4, 2018 (DE) .................. 10 2018 110 707.2
Aug. 1, 2018 (DE) .................. 10 2018 118 704.1

(51) Int. Cl.
*A61N 5/10* (2006.01)
*A61M 16/06* (2006.01)

(52) U.S. Cl.
CPC .............. *A61N 5/10* (2013.01); *A61M 16/06* (2013.01); *A61N 2005/1097* (2013.01)

(58) Field of Classification Search
CPC .... A61C 5/80; A61C 5/82; A61C 5/90; A61C 5/00; A61C 5/007; A45D 44/12;
(Continued)

(56) References Cited

U.S. PATENT DOCUMENTS

2002/0108616 A1* 8/2002 Woodburn, III ..... A61B 6/0421
128/861
2017/0333243 A1* 11/2017 Coppens ............... A61F 5/3707

FOREIGN PATENT DOCUMENTS

EP 2476375 A1 7/2012
WO 2014193938 A1 12/2014
WO WO-2014193938 A1 * 12/2014 ............. A61B 90/14

OTHER PUBLICATIONS

International Search Report and Written Opinion (with English translation of International Search Report) issued in corresponding International Patent Application No. PCT/EP2019/060440 dated Jul. 10, 2019 (10 pages).

* cited by examiner

*Primary Examiner* — Caitlin A Carreiro
(74) *Attorney, Agent, or Firm* — Kilyk & Bowersox, P.L.L.C.

(57) ABSTRACT

A device for immobilizing the head of a patient in an installation for carrying out radiotherapy is provided, wherein the device comprises a thermoplastic mask, shaped according to the contour of the patient's head, and a mouthpiece, wherein the mouthpiece has a central part from which a spout protrudes in the direction of the mouth and from which a holding structure protrudes in the direction away from the mouth, wherein an air channel is provided which extends through the mouthpiece from the mouth-side end of the spout to the side of the central part in the direction away from the mouth, and wherein a region of the mask is shaped according to the contour of the holding structure. A method for producing such a device, to the use of such a device and to an installation for carrying out radiotherapy which comprises such a device are also provided.

12 Claims, 10 Drawing Sheets

Figure 1:
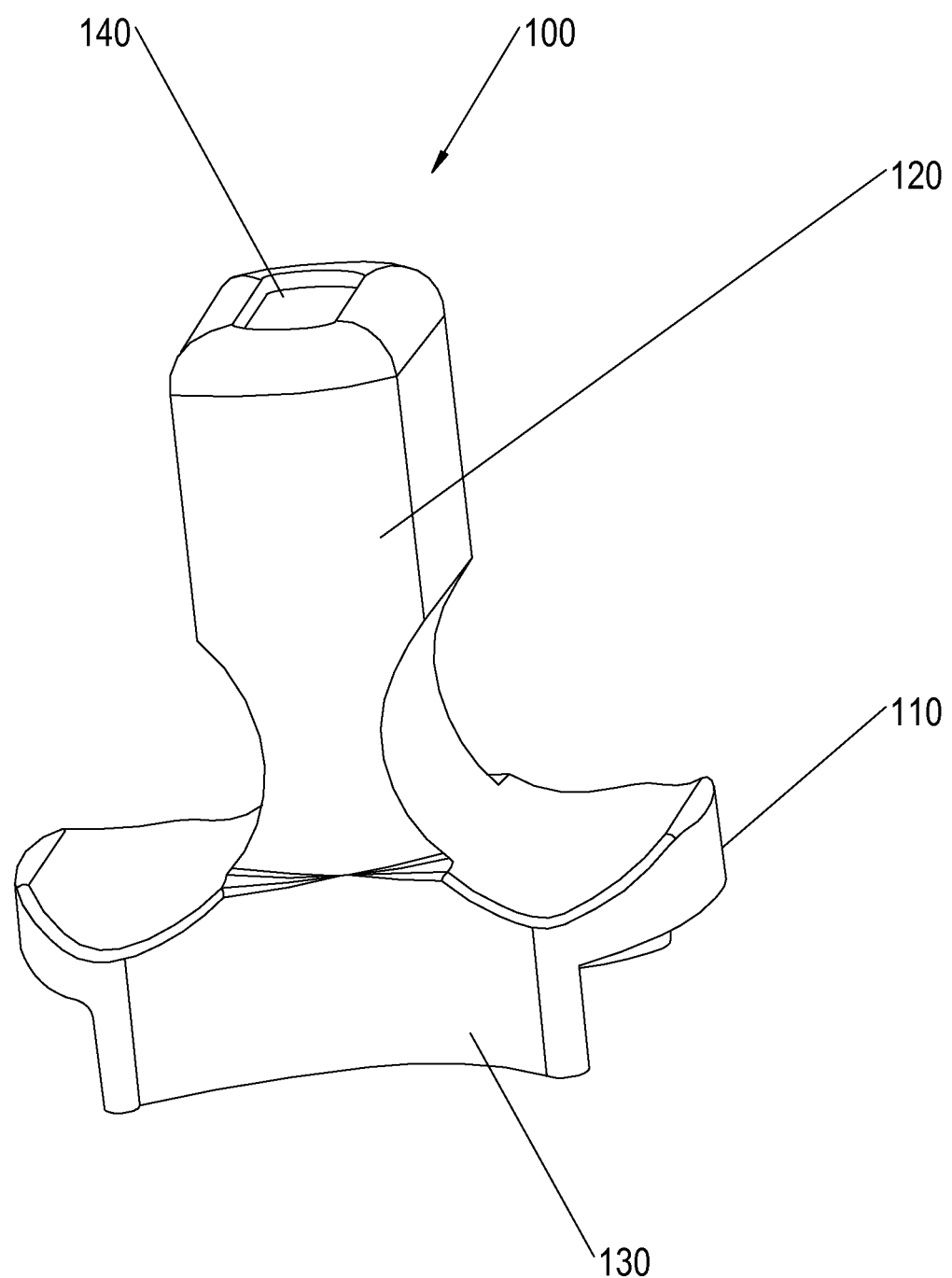

(58) Field of Classification Search
CPC ....... A61B 13/00; A61B 6/0421; A61B 6/501;
A61B 90/14; A61B 90/18; A61B 90/16;
A61B 90/10; A61F 2009/0035; A61F
9/026; A61F 9/029; A61F 9/02; A61F
5/3707; A61F 5/37; A61F 5/05883; A61F
5/05891; A61F 5/0104; A61M 16/06;
A61N 5/10; A61N 2005/1097
USPC ..... 606/130; 5/622, 636, 637; 128/845, 846,
128/857, 869
See application file for complete search history.

DEVICE FOR IMMOBILIZING THE HEAD OF A PATIENT

This application is a National Stage Application of PCT/EP2019/060440, filed Apr. 24, 2019, which claims priority to German Patent Application No. 10 2018 110 707.2, filed May 4, 2018 and German Patent Application No. 10 2018 118 704.1, filed Aug. 1, 2018.

The invention relates to a device and a method for immobilising the head of a patient in an installation for carrying out radiotherapy.

In a plurality of medical diagnosis and treatment methods, it is required that the head of a patient be secured in a precise and reproducible position. An example of such a treatment method is cranial radiotherapy, in which a brain tumour is to be irradiated. In particular, it is necessary in this case to immobilise the patient's head relative to a reference system that should be defined during pretreatment tomography. Moreover, when an ENT carcinoma is being irradiated, it may also be necessary for the jaw and tongue to be secured.

It is known in the prior art to use a thermoplastic mask that adjusts to the contours of the patient's head for this type of immobilising. To reproduce the original position during subsequent treatment steps, the mask is placed on the patient's head again and is secured in the same position in the treatment location or on the treatment table. Reference may be made by way of example to EP 2 476 375 A1 in this context.

To achieve increased accuracy in positioning the thermoplastic mask on the patient's head and to further reduce movements such as head movements and in particular jaw movements with the mask applied, a concept was presented in US 2002/108616 A1 in which a mouthpiece is secured on the thermoplastic mask. Among other things, however, this concept has the disadvantage that, in certain circumstances, the patient's breathing is impaired and the patient may become unwell or even panic.

It is an object of the invention to provide an improved concept for immobilising the patient's head, which overcomes the disadvantages of the prior art.

Against this background, the invention relates to a device for immobilising the head of a patient in an installation for carrying out radiotherapy, the device comprising a thermoplastic mask shaped according to the contour of the patient's head and a mouthpiece. According to the invention, it is provided that the mouthpiece has a central part from which a spout protrudes in the oral direction and from which a holding structure protrudes in the aboral direction, wherein an air channel is provided which passes through the mouthpiece from the mouth-side end of the spout to the aboral side of the central part, and in that a region of the mask is shaped according to the contour of the holding structure.

The holding structure extends out of the contact plane of the mask on the mouthpiece so that it can be reproduced in the mask. As a result of the corresponding shape of the holding structure of the mouthpiece on the one hand and of the corresponding shaping in the mask on the other hand, movement such as e.g. shifting or twisting of the mouthpiece in the contact plane of the mask is prevented. In particular, an accurate and reproducible position of the mouthpiece can be fixed in relation to the mask.

The spout serves on the one hand to define the air channel and on the other hand to secure the mouthpiece between the patient's jaws. Depending on whether an ENT tumour or a brain tumour is to be irradiated, the spout can be somewhat wider to hold the upper and lower jaw apart and press the tongue downwards, or somewhat narrower to increase comfort.

The thermoplastic mask is an originally flat sheet of material, which is heated and then shaped according to the contour of the patient's head and of the holding structure and which keeps this shape after cooling. The thermoplastic polymer material of the mask sheet is selected such that it becomes formable after heating to a working temperature of about 50° C. to no more than 100° C. and sets after cooling to a temperature lower than the working temperature, or in any case after cooling to below 40° C. Preferably, the mask is perforated in the manner of a sieve.

In one embodiment, it is provided that the thermoplastic mask material is mounted in a mask frame. The mask frame, for its part, can be secured at the treatment location of the installation, e.g. on a treatment table.

In one embodiment, it is provided that the mask frame has a U-shape and can be secured on a base plate which can be placed on the treatment table or represents part of the treatment table. The patient's head is then secured between the base plate and the thermoplastic mask material which is formed out of the plane of the mask frame. An example of such a system is disclosed in EP 2 476 375 A1.

The central part in one embodiment can be formed such that it serves as a limiter and can define the maximum penetration depth of the spout in the patient's mouth. In this context, it can be provided that the mouthpiece is not connected to the mask and sits with its holding structure loosely in the corresponding shaping in the mask. In this embodiment, therefore, no securing agents such as e.g. screws or latching elements are present to connect the mouthpiece to the mask. Likewise, no material connection, such as an adhesive bond or welded connection, is provided in this embodiment. The holding structure simply sits loosely in the corresponding shaping in the mask and can be pulled out of this shaping perpendicularly to the contact plane of the mask, readily and substantially without resistance. The shaping has no undercuts or the like to prevent or impede a relative movement perpendicular to the contact plane of the mask.

In one embodiment, it is provided that the holding structure has at least two structural elements protruding from the central part and/or that the structural element or elements of the holding structure have an elongated shape in the contact plane of the mask.

As a result of this shape, a multi-point fixing is achieved so that a rotation of the mouthpiece in relation to the mask is impossible and tilting is possible only with difficulty or not at all. The structural elements can comprise e.g. point-like pins or webs that are elongated in the contact plane of the mask, which preferably stand substantially perpendicular to the contact plane of the mask and therefore in the aboral direction.

In one embodiment, the structural elements comprise a merlon that protrudes from the central part in the axis of the spout, wherein the air channel continues to the aboral end of this merlon. The merlon in one embodiment can project at least slightly beyond all the other structural elements of the holding structure in the aboral direction. The securing of the mask on the mouthpiece can be improved by the merlon. Furthermore, by raising the outlet opening of the air channel from the base part, it is possible in the event of the patient's vomiting to avoid the return of the vomit into the air channel.

In one embodiment, the holding structure comprises at least three structural elements, namely two webs and a merlon of this type.

In one embodiment, it is provided that an aperture is incorporated in the region of the mask that is shaped according to the contour of the holding structure. Since the aboral opening of the air channel leading through the mouthpiece lies on the aboral side of the central part and therefore in the region of the holding structures, an aperture of this type is located in the region of the aboral opening of the air channel. Even if the mask material itself is already perforated in the manner of a sieve, the presence of a large aperture, in contrast to the small, regular perforation punchings, additionally facilitates breathing. In one embodiment, the merlon at least partially protrudes through the aperture.

In one embodiment, it is provided that the central part is a shield that extends in a manner substantially normal to the spout. In this embodiment, therefore, the mouthpiece comprises a central shield. When the device is in use, this should preferably be aligned substantially parallel to the patient's frontal plane and should therefore lie in the contact plane of the mask on the mouthpiece. It can have a circular or oval basic shape, for example.

In one embodiment, it is provided that the spout has a flattened shape. A flattened shape allows the patient to surround the spout comfortably with his lips and to bite on the spout with the jaw only slightly open. The flattened shape makes a significant contribution to patient comfort. In this embodiment, the device is suitable in particular for use during irradiation of a brain tumour.

In an alternative embodiment, it is provided that the height and width of the spout approximately correspond to one another. The more bulbous shape of the spout allows a specific positioning of the upper and lower jaw to be achieved and enables the tongue to be secured on the floor of the mouth. In this embodiment, the device is suitable in particular for use during irradiation of an ENT tumour.

In one embodiment, accommodating recesses are provided opposite one another on the spout and preferably in the transition region between spout and shield. These serve to accommodate the patient's lips and teeth.

In one embodiment, it is provided that the air channel comprises a bore, which preferably runs substantially perpendicular to the contact plane of the mask. The air channel enables the patient to breathe through the mouth despite having the spout in his mouth and surrounding it with his lips.

The invention furthermore relates to a method for producing a device according to the invention, wherein a flat and not yet shaped thermoplastic mask is heated until the mask material is formable, wherein the mask that has been thus heated is stretched over the head of a patient, who holds the spout of the mouthpiece in his mouth such that the holding structure is directed towards the mask material, and wherein the mask is then secured to a holder that is in a fixed position relative to the patient until it sets by cooling.

The mask can be actively cooled in the secured state, but it is preferable simply to wait until the mask cools by itself to below the softening point of the thermoplastic material. The holder can be mounted on a treatment table of an installation for carrying out radiotherapy, on which the patient is also positioned. While the mask is being stretched over the patient's head, the shapings or contours corresponding to the patient's head and to the holding structure are formed therein, and they are then fixed in the mask as a result of its setting. During the process as well as afterwards, no connection of the mask material to the mouthpiece preferably takes place. The mouthpiece and the mask are always present as separate parts, which can be separated and joined together by inserting the mouthpiece into the corresponding contour of the mask and removing it again therefrom.

Furthermore, the invention relates to the use of a device according to the invention for immobilising the head of a patient in an installation for carrying out radiotherapy. After it has been produced, the mask that has been shaped to the specific patient can be used in every subsequent immobilisation, e.g. in the context of diagnostic or therapeutic steps. It is provided in this case that the patient again holds the same or an identical mouthpiece in his mouth and the mask that has been kept since the production according to the invention is reapplied.

Finally, the invention also relates to an installation for carrying out radiotherapy which, in order to immobilise the head of a patient, comprises a device according to the invention. In one embodiment, the installation comprises a treatment table on which the thermoplastic mask is secured, optionally using a frame. The treatment table can have a base plate with means for securing the mask or frame, or can itself comprise such securing means.

Figure 2:
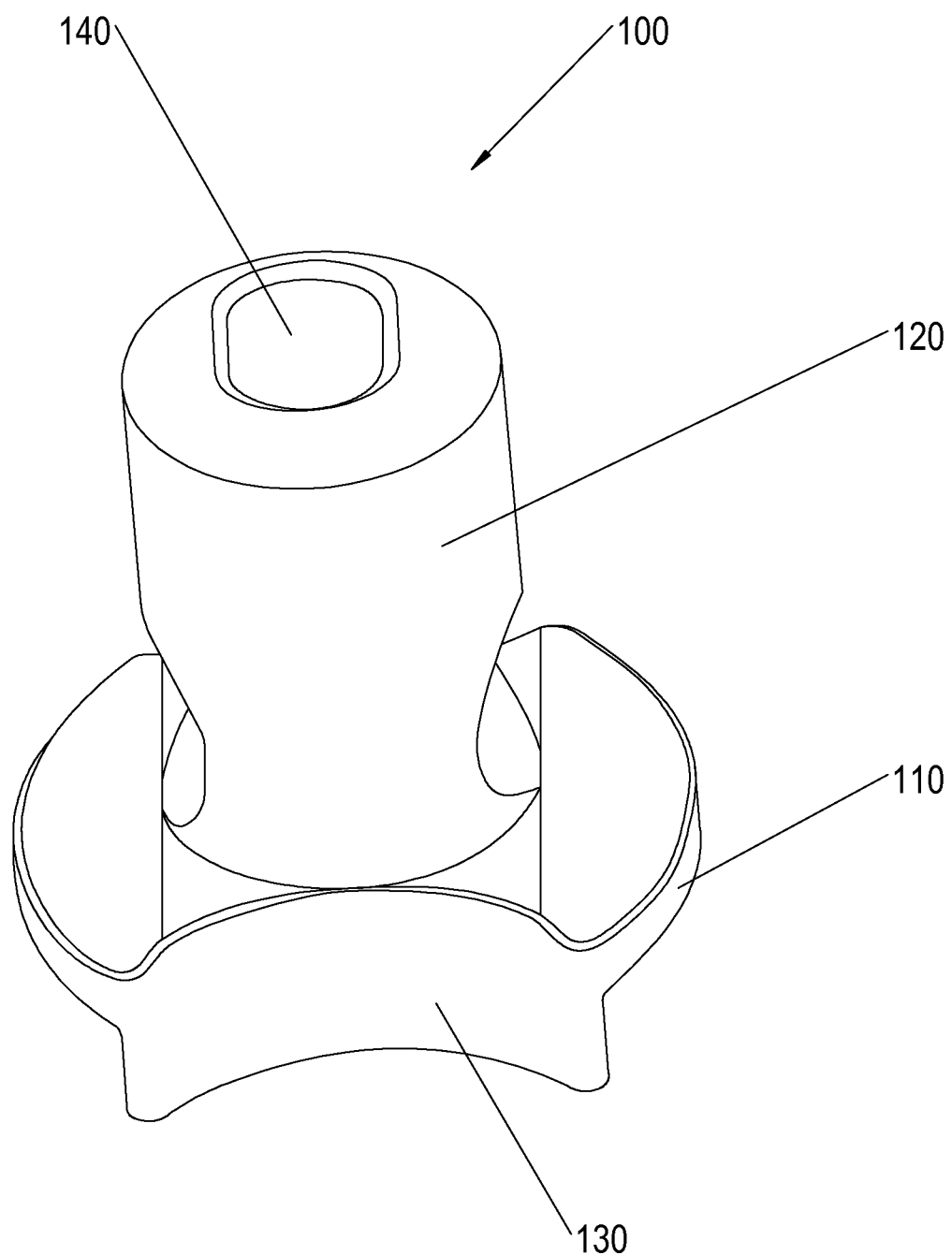

Further details and advantages of the invention can be taken from the following exemplary embodiment, which is explained below with reference to the figures. The figures show the following:

FIG. 1: a first embodiment of a mouthpiece of a device according to the invention;

FIG. 2: a second embodiment of a mouthpiece of a device according to the invention;

FIG. 3: views of a thermoplastic mask of a device according to the invention; and FIG. 4: a third embodiment of a mouthpiece of a device according to the invention.

In FIG. 1, a mouthpiece 100 of an embodiment of a device according to the invention is shown in a perspective view. The mouthpiece is suitable in particular for use during irradiation of a brain tumour.

The mouthpiece 100 comprises a central shield 110, which lies substantially parallel to the patient's frontal plane when the device is in use. In the example shown, it has a circular basic shape with partially circular indentations being provided on both the left-hand and right-hand upper sides. Starting from this shield 110, a horizontally flattened spout 120 extends in the oral direction. The width of the spout 120 in the example shown corresponds approximately to the distance between the vertices of the indentations. The spout 120 is held in the mouth by the patient during use. The shield 110 acts as a limiter and defines the penetration depth of the spout 120 in the patient's mouth, wherein in particular too deep a penetration is to be avoided.

In the transition region between spout 120 and shield 110, accommodating recesses 115 for lips and teeth are provided opposite one another. Owing to its special fit, the mouthpiece 100 is also suitable for toothless patients.

On its aboral side, the shield 110 is provided with a holding structure 130. In the example shown, the holding structure 130 comprises two webs protruding vertically from the shield, which follow the edge profile of the indentations in the shield 110. The contour of this holding structure 130 is reproduced in the mask 200 (FIG. 3) of the device during use in order that an accurate and reproducible position of the mouthpiece 100 can be fixed in relation to the mask 200.

The mouthpiece 100 further comprises an air channel 140, which extends from the mouth-side end of the spout 120 to the aboral side of the shield 110 and thus passes through the mouthpiece 100 from the oral side to the aboral side. The air channel 140 enables the patient to breathe through the mouth despite having the spout 120 in his mouth and surrounding it with his lips. In the example shown, the air channel 140 comprises a single bore.

In FIG. 2, a mouthpiece 100 of a further embodiment of a device according to the invention is shown in a perspective view. The mouthpiece 100 of FIG. 2 is suitable in particular for use in the irradiation of an ENT tumour. Identical reference numerals are used for corresponding parts in FIG. 2. The mouthpiece 100 of FIG. 2 differs from the mouthpiece of FIG. 1 by the shape of the spout 120, which is more bulbous and approximately round in its cross-section. This alternative shape allows a specific positioning of the upper and lower jaw to be achieved and enables the tongue to be secured on the floor of the mouth.

Figure 3A:
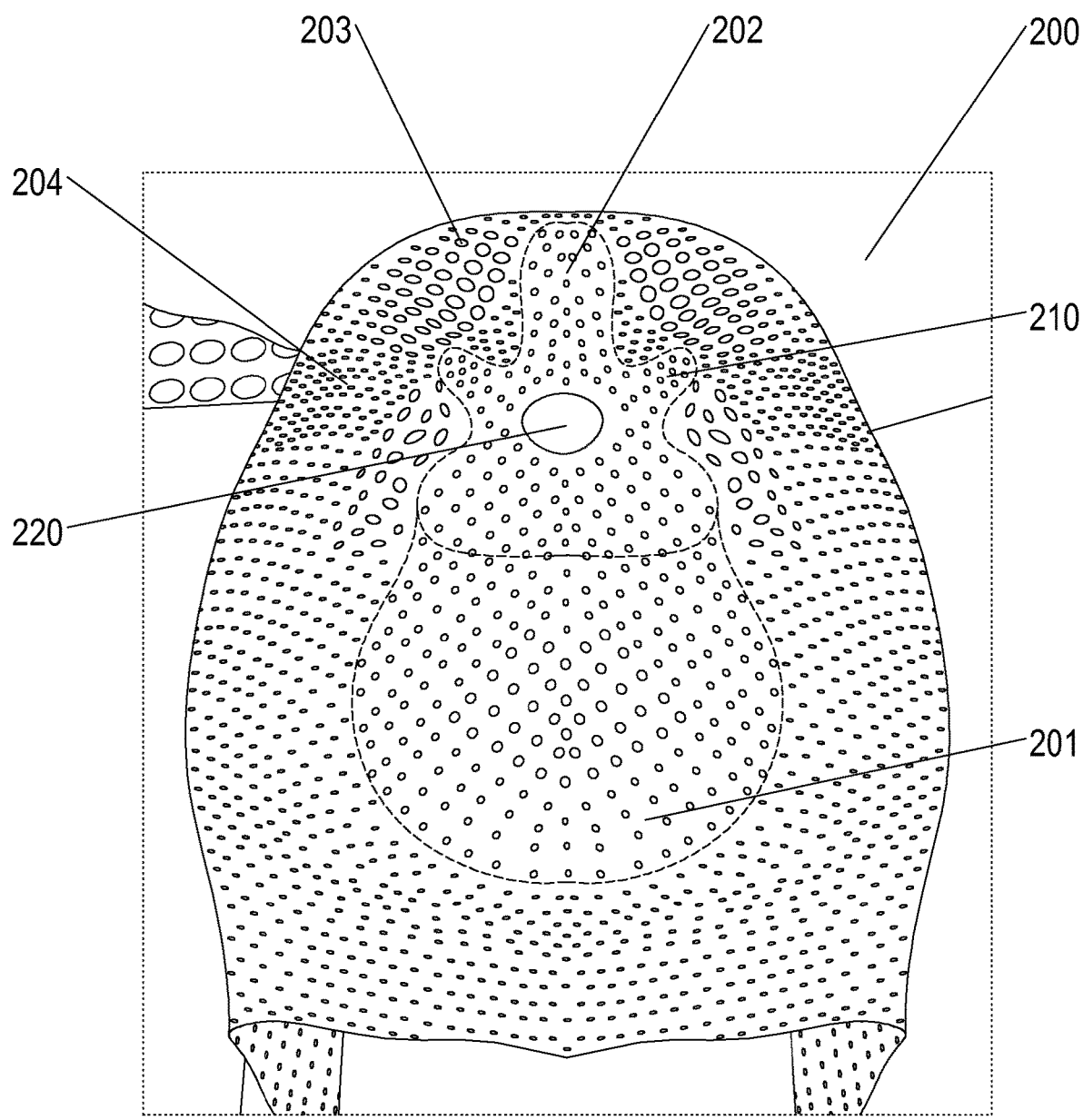
Figure 3B:
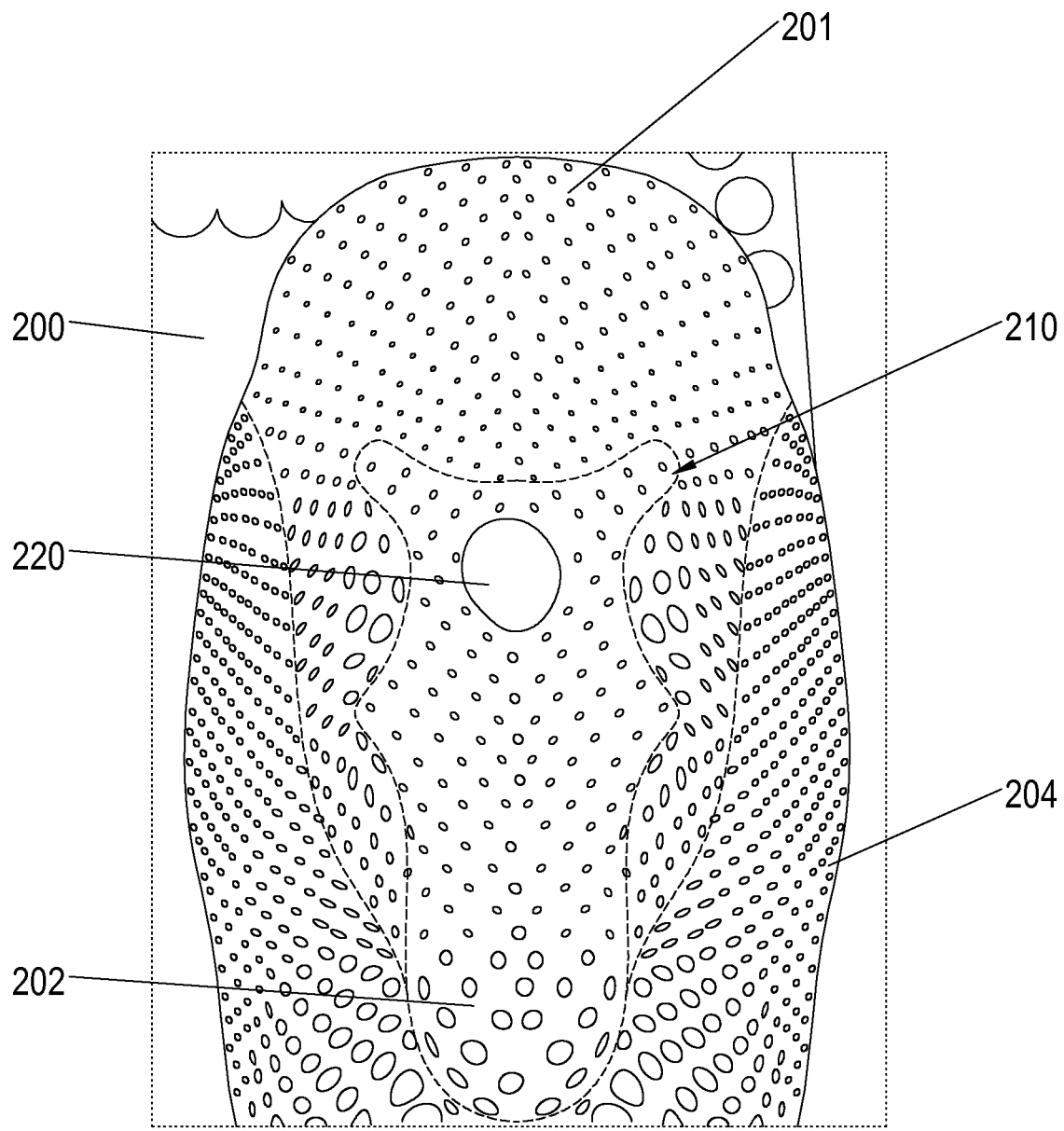
Figure 3C:
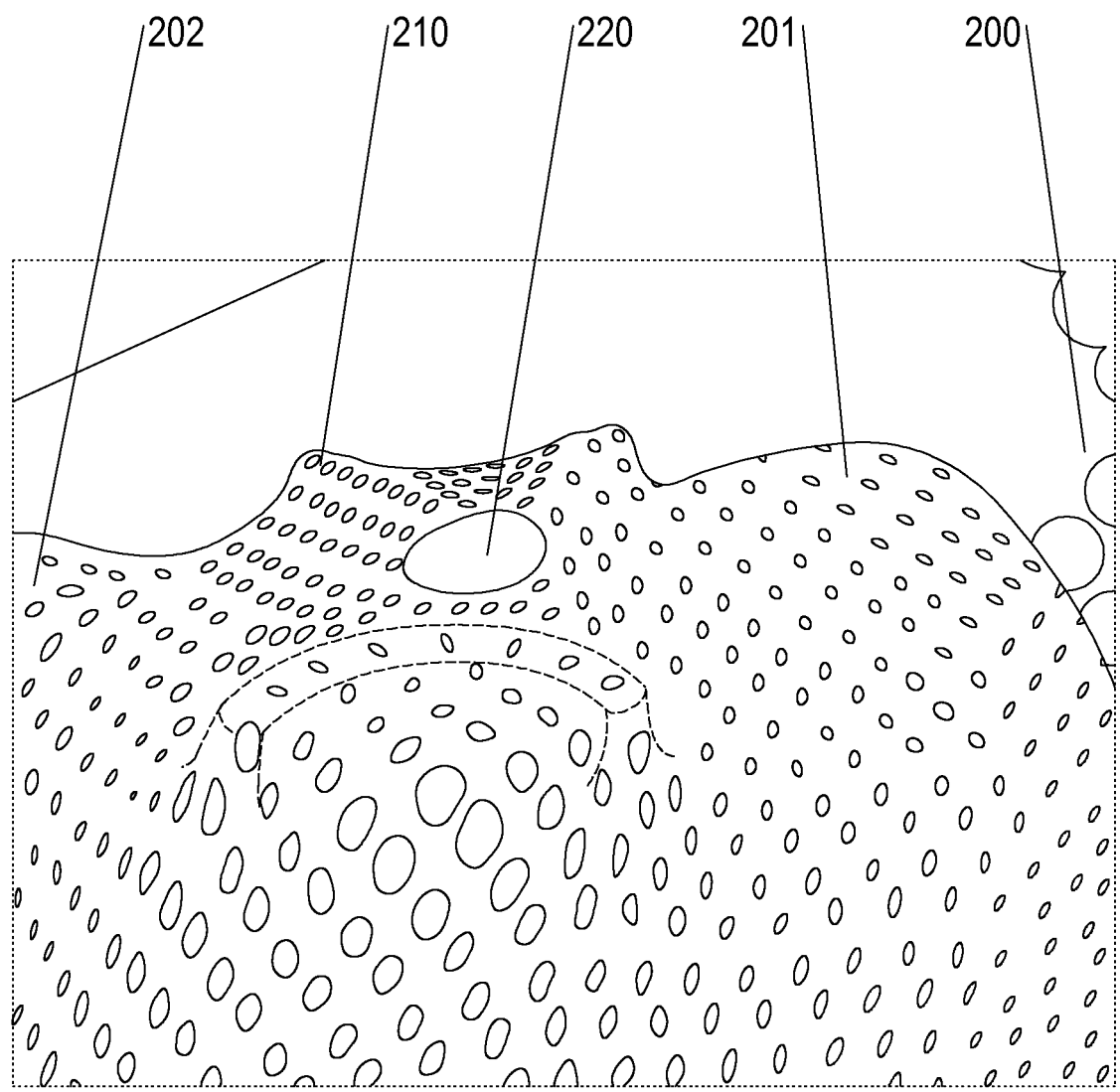

In FIGS. 3a-3c, a mask 200 of an embodiment of a device according to the invention is shown from multiple perspectives. FIG. 3a shows the mask 200—with reference to the patient—at an angle from below, FIG. 3b at an angle from above and FIG. 3c at an angle from the right.

The mask 200 is represented by a leaf-like sheet of a thermoplastic polymer material, which has been shaped according to the contour of the patient's head. In the figures, inter alia, contours corresponding to the chin (reference numeral 201), nose (reference numeral 202), forehead (reference numeral 203) and cheeks (reference numeral 204) can be seen. The sheet is penetrated by closely spaced small holes, such that it has an almost net-like structure. This increases patient comfort and enables the patient to perceive his surroundings. Furthermore, the shaping of the originally flat sheet is facilitated by the holes. The sheet representing the mask 200 is mounted at the rear end, as can be partially seen in FIG. 3a, in a mask frame 300, which can be secured on a treatment table (not shown) of an installation for carrying out radiotherapy.

In the region of the sheet that covers the patient's mouth region, a mouthpiece contour 210 can be seen, which corresponds to the holding structure 130 of the mouthpiece 100 (FIG. 1 or 2). With the aid of this mouthpiece contour 210, an accurate and reproducible position of the mouthpiece 100 can be fixed in relation to the mask 200. In the example shown, the mouthpiece contour 210 has an X-like shape, which is obtained as a necessary consequence of the shape of the holding structure 130 of the mouthpiece 100. The four retention points at the corner edges here facilitate a non-rotatable fixing.

At a point of the mask 200 that lies directly over the patient's mouth during use, an aperture is incorporated. It therefore lies approximately in the centre of the mouthpiece contour 210. In the example shown, the aperture 220 is approximately circular. Thanks to the aperture 220, the air channel 140 of the mouthpiece 100 (FIG. 1 or 2) is unobstructed during use of the device and the patient's breathing is not impaired.

With the aid of the device shown, an immobilising of the head of a patient can take place in an installation for carrying out radiotherapy.

During the initial fitting, the patient first holds the spout 120 of the mouthpiece 100 in his mouth such that the recesses 115 are enclosed between teeth and lips. Next, as known in principle from the prior art, the mask 200 with heated mask material is stretched over the patient's head so that the contour of the patient's head is shaped in the originally flat mask material. In contrast to the prior art, however, not only is the contour of the patient's head reproduced in the mask material but additionally the holding structure 130 of the mouthpiece 100 as a mouthpiece contour 220. The mask material then hardens by cooling. Once the mask material has hardened, the mask 200 is taken off the patient and the mouthpiece 100 is removed from the patient. The aperture 220 is cut out afterwards. The mask 200 with the hardened mask material that has been shaped for the specific patient is stored for further immobilisations. The mouthpiece 100 may be either cleaned for reuse or disposed of.

In every further immobilising, e.g. in the context of diagnostic or therapeutic steps, the patient again holds the same or an identical mouthpiece 100 in his mouth and the mask 200 that has been kept since the initial fitting described above, with the hardened mask material that has been shaped for the specific patient, is reapplied.

With the aid of this novel system, high positioning accuracy of the mask 200 on the patient's head can be achieved and head movements and in particular jaw movements can be largely avoided. At the same time, the patient's breathing is scarcely impaired and patient comfort is improved compared to existing solutions.

Figure 4A:
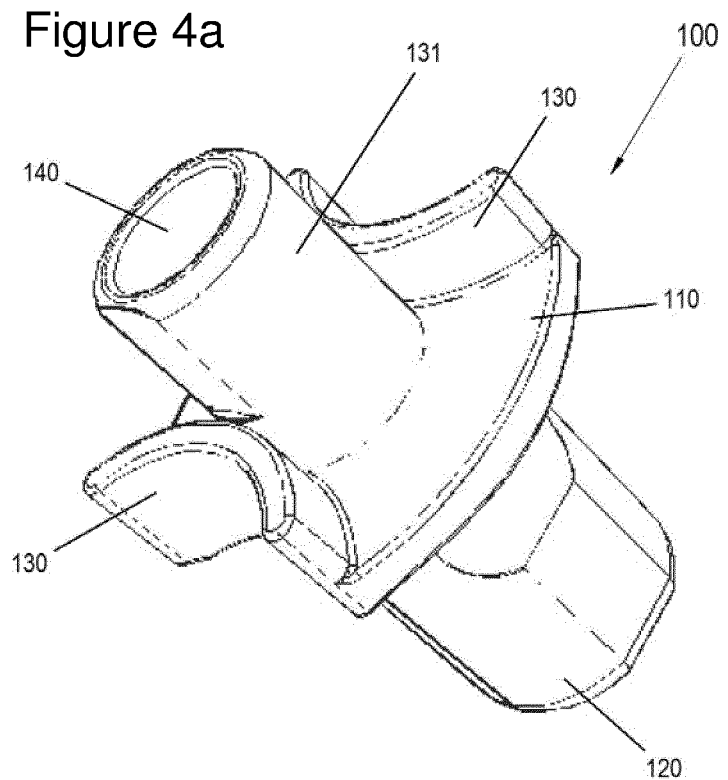
Figure 4B:
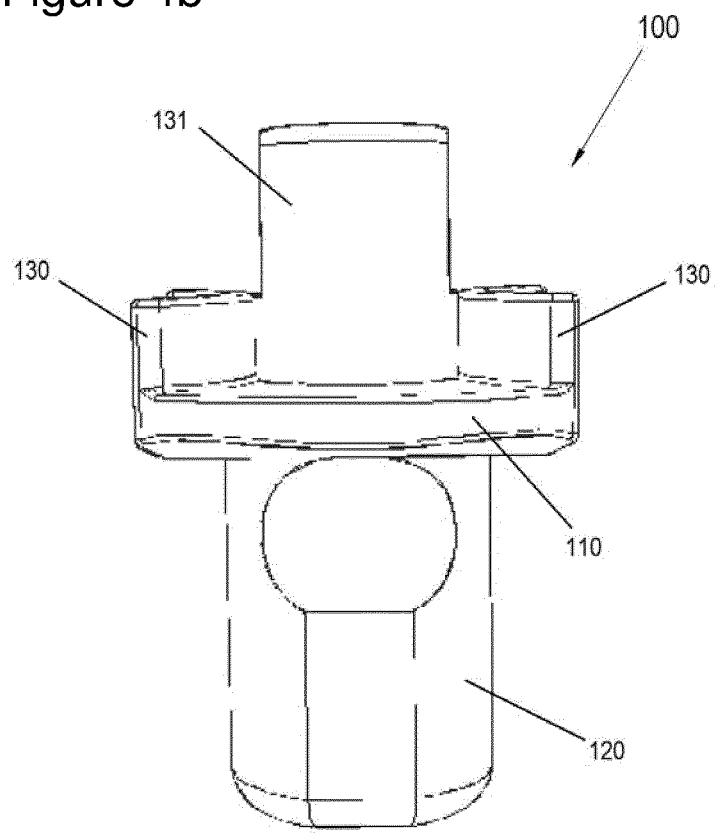
Figure 4C:
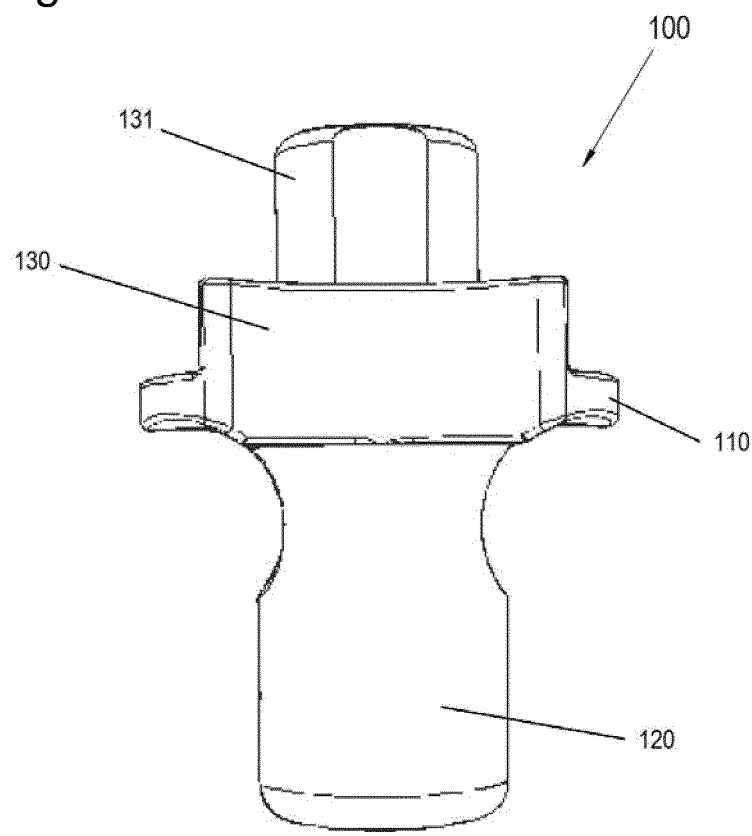
Figure 4D:
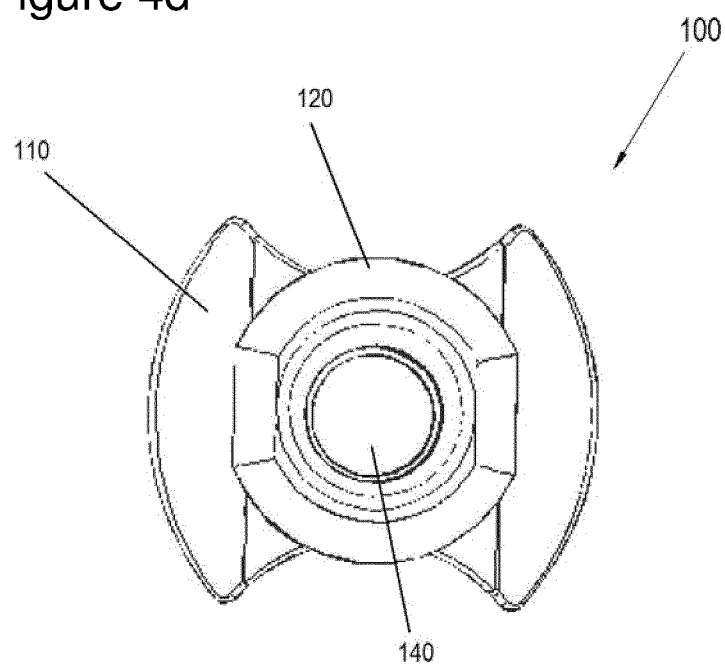
Figure 4E:
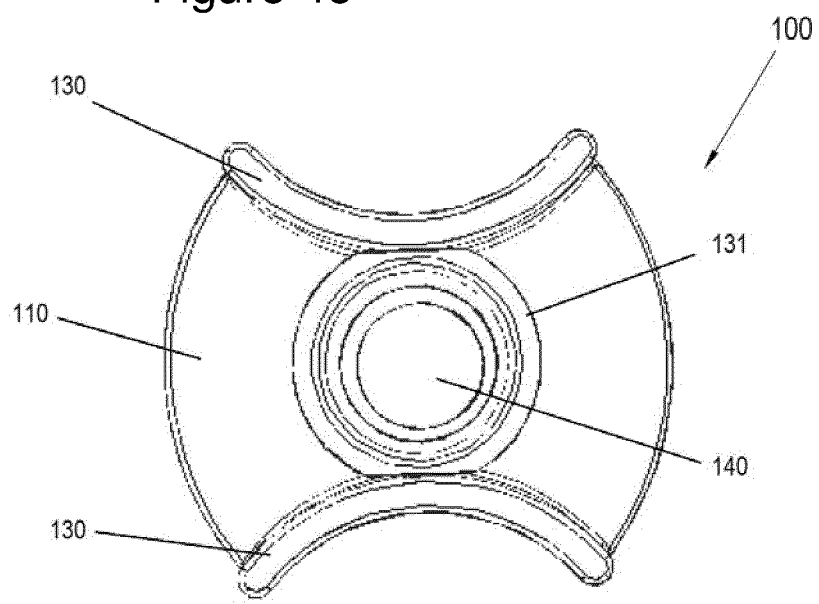

Finally, FIGS. 4a-4e show a further embodiment of a mouthpiece 100 of a device according to the invention, and specifically in a perspective illustration (FIG. 4a), in side views (FIGS. 4b-c) and as top views from the oral side (FIG. 4d) and from the aboral side (FIG. 4e).

The mouthpiece 100 of the embodiment according to FIG. 4 is very similar to the mouthpiece of the embodiment according to FIG. 2 in principle. The only differentiating feature is the additional aboral holding structure in the form of a merlon 131, which protrudes vertically from the central part 110 in the axis of the spout and clearly projects beyond the webs 130 in the aboral direction. The air channel 140 in this embodiment continues to the aboral end of the merlon 131 and therefore does not already terminate on the aboral side of the shield 110.

By using the merlon 131, the securing of the mask 200 on the mouthpiece 100 can be improved. Furthermore, by raising the outlet opening of the air channel 140 from the shield 110, in the event of the patient's vomiting, the vomit is prevented from being able to pass back into the air channel 140. The merlon 131 can in some circumstances project at least partially through the aperture 220 when the mask 200 is applied; however, it is preferred for the mask material to be shaped such that the aperture 220 rests on the tip of the merlon 131.

The invention claimed is:

1. A device for immobilising a head of a patient in an installation for carrying out radiotherapy, wherein the device comprises a thermoplastic mask shaped according to a contour of the head of the patient and a mouthpiece, wherein the mouthpiece has a central part from which a spout protrudes in an oral direction and from which a holding structure protrudes in an aboral direction, wherein an air channel is provided which passes through the mouthpiece from a mouth-side end of the spout to an aboral side of the central part, and in a region of the thermoplastic mask that is configured to cover a mouth region of said patient, a mouthpiece contour is shaped according to a contour of the holding structure, such that the thermoplastic mask is configured to lie over said mouth region of said patient and the holding structure of the mouthpiece, and wherein the mouthpiece is not connected to the thermoplastic mask and sits with the holding structure loosely in a corresponding shaping in the thermoplastic mask.

2. The device according to claim 1, wherein the holding structure has at least two structural elements protruding from the central part and/or in that one or more structural elements of the holding structure have an elongated shape in a contact plane of the thermoplastic mask.

3. The device according to claim 2, wherein the one or more structural elements comprise a merlon protruding from the central part in an axis of the spout, wherein the air channel continues to an aboral end of the merlon.

4. The device according to claim 1, wherein the central part is a shield, which extends in a manner substantially normal to the spout.

5. The device according to claim 4, wherein accommodating recesses are provided opposite one another on the spout in a transition region between said spout and said shield.

6. The device according to claim 1, wherein an aperture is incorporated in the region of the thermoplastic mask that is shaped according to the contour of the holding structure.

7. The device according to claim 1, wherein accommodating recesses are provided opposite one another on the spout.

8. The device according to claim 1, wherein the air channel comprises a bore.

9. The device according to claim 1, wherein the air channel comprises a bore, which runs substantially perpendicular to a contact plane of the thermoplastic mask.

10. A method for producing a device according to claim 1, wherein a flat and not yet shaped thermoplastic mask is heated until the material of the thermoplastic mask is formable, wherein the thermoplastic mask that has been heated is stretched over the head of a patient, who holds the spout of the mouthpiece in their mouth such that the holding structure is directed towards the material of the thermoplastic mask, and in that the thermoplastic mask is then secured to a holder that is in a fixed position relative to the patient until it sets by cooling.

11. A method for immobilising a head of a patient in an installation for carrying out radiotherapy, said method comprising immobilising said head with the device of claim 1, said immobilising comprising: placing the mouthpiece in a mouth of said patient; applying the thermoplastic mask over the mouthpiece and said head of said patient; and securing the thermoplastic mask to a treatment table.

12. A method for carrying out radiotherapy on a patient, said method comprising immobilising a head of said patient with the device of claim 1, said immobilising comprising: placing the mouthpiece in a mouth of said patient; applying the thermoplastic mask over the mouthpiece and said head of said patient; and securing the thermoplastic mask to a treatment table, and then conducting said radiotherapy on said patient.

* * * * *